(12) United States Patent
Hani et al.

(10) Patent No.: US 9,884,822 B2
(45) Date of Patent: Feb. 6, 2018

(54) PROCESS FOR THE PREPARATION OF 1-HYDROXY-6-SUBSTITUTED PYRIDONES

(71) Applicant: Arch Chemicals, Inc., Atlanta, GA (US)

(72) Inventors: Rahim Hani, Alpharetta, GA (US); David A. Steele, Webster, NY (US); John Joseph Jardas, Rochester, NY (US)

(73) Assignee: Arch Chemicals, Inc., Atlanta, GA (US)

( * ) Notice: Subject to any disclaimer, the term of this patent is extended or adjusted under 35 U.S.C. 154(b) by 175 days.

(21) Appl. No.: 13/763,328

(22) Filed: Feb. 8, 2013

(65) Prior Publication Data

US 2013/0211093 A1 Aug. 15, 2013

Related U.S. Application Data

(60) Provisional application No. 61/596,751, filed on Feb. 9, 2012.

(51) Int. Cl.
| | |
|---|---|
| C07D 211/72 | (2006.01) |
| C07D 211/84 | (2006.01) |
| C07D 213/69 | (2006.01) |
| C07D 213/70 | (2006.01) |
| C07D 213/61 | (2006.01) |
| A61K 31/50 | (2006.01) |
| A61K 31/495 | (2006.01) |
| C07D 211/94 | (2006.01) |
| C07D 213/89 | (2006.01) |

(52) U.S. Cl.
CPC .......... *C07D 211/94* (2013.01); *C07D 213/61* (2013.01); *C07D 213/89* (2013.01)

(58) Field of Classification Search
None
See application file for complete search history.

(56) References Cited

U.S. PATENT DOCUMENTS

| | | | |
|---|---|---|---|
| 2,540,218 A | 2/1951 | Shaw | |
| 5,240,566 A * | 8/1993 | Hahn | B01D 3/36 203/12 |
| 5,424,435 A | 6/1995 | Hani et al. | |
| 2011/0005915 A1* | 1/2011 | Mercier | B01D 3/36 203/51 |

FOREIGN PATENT DOCUMENTS

| | | |
|---|---|---|
| EP | 0724571 | 8/1996 |
| EP | 2524917 | 11/2012 |
| WO | WO 1995/011233 A * | 4/1995 |
| WO | WO 2006115652 | 11/2006 |
| WO | WO 2011085643 | 7/2011 |

OTHER PUBLICATIONS

Evans, DA. et al. Chiral Bis(oxazoline)copper(II) Complexes as Lewis Acid Catalysts for the Enantioselective Diels-Alder Reaction. J. Am. Chem. Soc. 1999, vol. 121, p. 7559.*
Toste, FD. et al. Chiral Brønsted Acid from a Cationic Gold(I) Complex: Catalytic Enantioselective Protonation of Silyl Enol Ethers of Ketones. J. Am. Chem. Soc. 2011, vol. 133, p. 13249.*
Suschitzky, KV. et al. Polyhalogeno-aromatic Compounds. Part XXI. A Novel Reagent System for the N-Oxidation of Weakly Basic N-Heteroaromatic Compounds. J. Chem. Soc. 1971, p. 2867.*
International Search Report and Written Opinion for PCT/US2013/025314, dated May 14, 2013.
Rousseau, Robert J. et al., "The synthesis of various chloroimidazo[4,5-c]pyridines and related derivatives," Journal of Heterocyclic Chemistry, vol. 2, No. 2, pp. 196-201 (1965). (Abstract).
Zhu, Guang-Hui et al., "Synthesis and characterization of a novel polyimide ionomer," Journal of Functional Polymers, vol. 23, pp. 115-120 (2010). (Abstract).
Wang, Chuanqing et al., "Fast Catalytic Hydroxylation of Hydrocarbons with Ruthenium Porphyrins," Inorganic Chemistry, vol. 45, No. 12, pp. 4769-4782 (2006). (Abstract).
Suschitzky, H. et al., "Polyhaloaromatic compounds. XXI. Novel reagent systems for the N-oxidation of weakly basic N-heteroaromatic compounds," Journal of the Chemical Society, Section C: Organic, pp. 2867-2871 (1971) (Abstract).

* cited by examiner

Primary Examiner — Andrew D Kosar
Assistant Examiner — Ben S Michelson
(74) Attorney, Agent, or Firm — Dority & Manning, P.A.

(57) ABSTRACT

Disclosed herein is a cost effective and environmentally friendly process to prepare 1-hydroxy-6-substituted pyridones from 2,6-dichloropyridine. The process includes the steps of (a) reacting 2,6-dichloropyridine with hydrogen peroxide in the presence of trifluoroacetic acid at a first temperature to produce a first intermediate containing (1) trifluoroacetic acid and (2) 2,6-dichloropyridine N-oxide and/or salts thereof; (b) adding sulfuric acid to the first intermediate to provide a second intermediate; (c) removing trifluoroacetic acid from the second intermediate to provide a composition containing 2,6-dichloropyridine N-oxide and/or salts thereof which is essentially free of trifluoroacetic acid; (d) reacting 2,6-dichloropyridine N-oxide and/or salts thereof from step (c) with RXH and a base wherein each R is independently a substituted or unsubstituted hydrocarbyl group having between 1 and 20 carbon atoms, X is oxygen or sulfur, to produce a corresponding 2,6-disubstituted-pyridine N-oxide; and (e) heating the disubstituted compound thereby producing the 1-hydroxy-6-substituted pyridone.

23 Claims, No Drawings

PROCESS FOR THE PREPARATION OF 1-HYDROXY-6-SUBSTITUTED PYRIDONES

RELATED APPLICATIONS

The present application claims filing benefit of U.S. Provisional Patent Application Ser. No. 61/596,751 having a filing date of Feb. 9, 2012, and which is incorporated herein in its entirety.

FIELD OF THE INVENTION

The present invention generally relates to a process for the preparation of 1-hydroxy-6-substituted pyridones, particularly it relates to a cost effective and environmentally friendly process for the preparation of 1-hydroxy-6-(octyloxy)pyridine-2(1H)-one from 2,6-dichloropyridine in good yield and high purity. The present invention also relates to the oxidation of 2,6-dichloropyridine, the recovery and reuse of the trifluoroacetic acid from the oxidation process.

BACKGROUND OF THE INVENTION

1-Hydroxy-6-substituted pyridones are known biocides. Although these pyridones exhibit excellent biocidal activity, and can be used in soaps, shampoos, skin care medicaments, cosmetics, adhesives, coatings, elastomers, sealants, wood, plastics and paints, currently their use in commercial products is limited because the pyridones are more expensive to manufacture than otherwise might be desired.

Heretofore 1-hydroxy-6-substituted pyridones are prepared from 2,6-dichloropyridine-N-oxide. As disclosed in U.S. Pat. No. 5,424,435, the process includes the steps of: (a) reacting 2,6-dichloropyridine-N-oxide, a hydroxy compound containing between 1 and 20 carbon atoms, and a base, optionally in the presence of water or an organic solvent, at an elevated temperature to produce a corresponding 2-chloro-6-substituted-pyridine-N-oxide, and (b) reacting the 2-chloro-6-substituted-pyridine-N-oxide with additional base to produce the corresponding 1-hydroxy-6-substituted pyridone.

One disadvantage associated with the prior art process is the low yield. Illustratively, at example 4 of U.S. Pat. No. 5,424,435, the patentees described the synthesis of 1-hydroxy-6-octyloxypyridine-2-(1H)-one from 2,6-dichloropyridine-N-oxide and 1-octanol at a 1:1 molar ratio in the presence of sodium hydroxide. The yield for the reaction was only 48%. In addition, in order to obtain a product of acceptable purity, the 1-hydroxy-6-(octyloxy)pyridine-2-(1H)-one has to be purified by recrystallization from ethanol and hexane. Such purification is cumbersome in the industrial settings and adds cost to the manufacturing process.

Methods to prepare 2,6-dichloropyridine-N-oxide, the starting material for the 1-hydroxy-6-substituted-pyridine-2 (1H)-one, are known. Illustratively, it can be prepared by reacting dichloropyridine with hydrogen peroxide in the presence of trifluoroacetic acid. See Robert J. Rousseau and Roland K. Robins, Journal of Heterocyclic Chemistry, vol. 2, 196-201, 1965; and G. Zhu et al., Journal of Functional Polymers, vol. 23, 115-120, 2010. However, the prior art process used large amounts of trifluoroacetic acid, which could not be completely distilled off and had to be neutralized thus wasting expensive trifluoroacetic acid and producing byproducts that are potentially hazardous to the environment. Further, the prior art oxidation process gave only moderate yields of 2,6-dichloropyridine-N-oxide.

Accordingly, there is a continuing need in the biocide manufacturing industry for a cost effective and environmentally friendly processes to prepare 1-hydroxy-6-substituted pyridones and 2,6-dichloropyridine-N-oxide. The present invention is believed to provide an answer to that need.

SUMMARY OF THE INVENTION

In general, the present disclosure is directed to a process for separating an acid catalyst from a pyridine oxide, such as during production of the pyridine oxide.

In one embodiment, the present disclosure is directed to a process for separating (1) an acid catalyst and (2) 2,6-dichloropyridine-N-oxide and/or salts thereof from a composition containing (1) the acid catalyst and (2) 2,6-dichloropyridine-N-oxide and/or salts thereof, the process comprising adding an acid having a pKa number lower than the pKa number of the acid catalyst to the a composition containing (1) an acid catalyst and (2) 2,6-dichloropyridine-N-oxide and/or salts thereof; and removing the acid catalyst.

In an alternative embodiment, the present disclosure is directed to a process for producing the compound of the structural Formula (I)

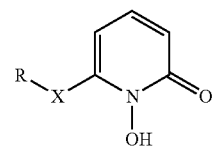

wherein X is oxygen or sulfur, each R is independently a substituted or unsubstituted hydrocarbyl group having between 1 and 20 carbon atoms, the process comprising the steps of:

(a) reacting 2,6-dichloropyridine with hydrogen peroxide in the presence of an acid catalyst at a first temperature to produce a first intermediate containing (1) the acid catalyst and (2) 2,6-dichloro-pyridine-N-oxide and/or salts thereof;

(b) adding an acid having a pKa number lower than the pKa number of the acid catalyst to the first intermediate to provide a second intermediate;

(c) removing the acid catalyst from the second intermediate to provide a composition containing 2,6-dichloropyridine-N-oxide and/or salts thereof;

(d) reacting 2,6-dichloropyridine-N-oxide and/or salts thereof from step (c) with a compound having the structural formula (II), and a base, optionally in the presence of water or an organic solvent, at a second temperature to produce a compound of Formula (III); and (e) heating the compound of Formula (III) at a third temperature thereby producing the compound of Formula (I), wherein the compounds of Formula (II) and Formula (III) are:

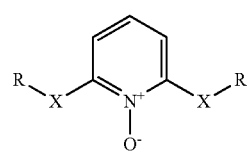

(Formula II)

(Formula III)

wherein each R in Formulae (II) and (III) is independently a substituted or unsubstituted hydrocarbyl group having between 1 and 20 carbon atoms, and X is oxygen or sulfur.

In one embodiment, the acid catalyst may comprise trifluoroacetic acid, while the acid having a pKa number lower than the pKa number of the acid catalyst may be sulfuric acid.

In one aspect, the present invention relates to a process for separating (1) trifluoroacetic acid and (2) 2,6-dichloropyridine-N-oxide and/or salts thereof from a composition containing (1) trifluoroacetic acid and (2) 2,6-dichloropyridine-N-oxide and/or salts thereof. The process includes the steps of:

(a) providing a composition containing (1) trifluoroacetic acid and (2) 2,6-dichloropyridine-N-oxide and/or salts thereof;

(b) adding sulfuric acid to the composition; and (c) removing trifluoroacetic acid.

In another aspect, the present invention is directed to a process for producing a composition containing 2,6-dichloropyridine-N-oxide and/or salts thereof, which is essentially free of trifluoroacetic acid, the process comprising the steps of:

(a) reacting 2,6-dichloropyridine with hydrogen peroxide in the presence of trifluoroacetic acid at an elevated temperature to produce a crude product containing (1) trifluoroacetic acid and (2) 2,6-dichloropyridine-N-oxide and/or salts thereof;

(b) adding sulfuric acid to the crude product to provide a mixture; and (c) removing trifluoroacetic acid from the mixture of step (b) thereby producing the composition containing 2,6-dichloropyridine-N-oxide and/or salts thereof, which is essentially free of trifluoroacetic acid.

In yet another aspect, the present invention relates to a process for producing the compound of the structural formula (I)

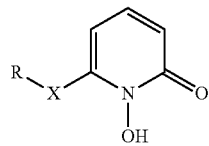

(I)

wherein X is oxygen or sulfur, each occurrence of R is independently a substituted or unsubstituted hydrocarbyl group having between 1 and 20 carbon atoms. The process includes the steps of:

(a) reacting 2,6-dichloropyridine with hydrogen peroxide in the presence of trifluoroacetic acid at a first temperature to produce a first intermediate containing (1) trifluoroacetic acid and (2) 2,6-dichloropyridine-N-oxide and/or salts thereof;

(b) adding sulfuric acid to the first intermediate to provide a second intermediate;

(c) removing trifluoroacetic acid from the second intermediate to provide a composition containing 2,6-dichloropyridine and/or salts thereof, (d) reacting 2,6-dichloropyridine-N-oxide and/or salts thereof from step (c) with a compound having the structural formula (II), and a base, optionally in the presence of water or an organic solvent, at a second temperature to produce a compound of Formula (III); and (e) heating the compound of Formula (III) at a third temperature thereby producing the compound of Formula (I), wherein the Formula (II) and Formula (III) are:

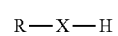

(Formula II)

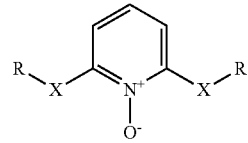

(Formula III)

wherein X is oxygen or sulfur, each R in Formulae (II) and (III) is independently a substituted or unsubstituted hydrocarbyl group having between 1 and 20 carbon atoms.

These and other aspects will become apparent upon reading the detailed description of the invention.

DETAILED DESCRIPTION

It has now been surprisingly found that 1-hydroxy-6-substituted pyridones can be produced from 2,6-dichloropyridine, a readily available commercial product, through a cost-effective and environmentally friendly process. The improved process allows 1-hydroxy-6-substituted pyridones to be manufactured at a reasonable price, thus making it more affordable for commercial applications.

1-Hydroxy-6-substituted pyridones can be represented by structural Formula (I):

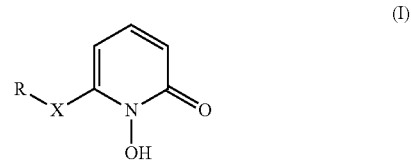

(I)

In connection with Formula (I), X is an oxygen or sulfur and each occurrence of R is independently a substituted or unsubstituted hydrocarbyl group having between 1 and 20 carbon atoms. Preferred hydrocarbyl groups are aliphatic hydrocarbyl groups having between 3 and 18 carbons, more preferably straight chain hydrocarbyl groups having between 5 and 10 carbons. As used herein, the term "substituted hydrocarbyl group" is intended to include hydrocarbyl groups bearing substituents such as halogen, for example, alkyl, aryl, chloro, iodo, fluoro or bromo, alkoxy such as methoxy, ethoxy, propoxy or butoxy, nitro, thio, and the like. Illustrative hydrocarbyl groups include n-octyl, 2,4,4-trimethylpentyl, 3,5,5-trimethylhexyl and the like. One preferred 1-hydroxyl-6-substituted pyridone is 1-hydroxy-6-octyloxypyridine-2-(1H)-one.

The process of producing the compound of Formula (I) includes the steps of (a) reacting 2,6-dichloropyridine with hydrogen peroxide in the presence of trifluoroacetic acid at a first temperature to produce a first intermediate containing (1) trifluoroacetic acid and (2) 2,6-dichloropyridine-N-oxide and/or salts thereof; (b) adding sulfuric acid to the first intermediate to provide a second intermediate; (c) removing trifluoroacetic acid from the second intermediate to provide a composition containing 2,6-dichloropyridine-N-oxide and/or salts thereof, (d) reacting 2,6-dichloropyridine-N-oxide and/or salts thereof from step (c) with a compound having the structural formula (II), and a base, optionally in the presence of water or an organic solvent, at a second temperature to produce a compound of Formula (III); and (e) heating the compound of Formula (III) at a third temperature thereby producing the compound of Formula (I).

The compounds of Formula (II) and Formula (III) are:

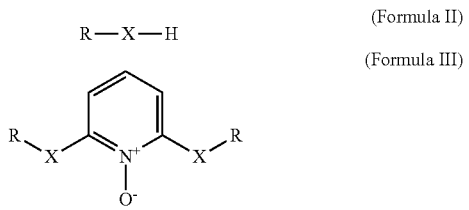

wherein each R in Formulae (II) and (III) is independently a substituted or unsubstituted hydrocarbyl group having between 1 and 20 carbon atoms. In one embodiment, R is octyl, and X is oxygen in Formulae (I), (II) and (III).

At step (a), 2,6-dichloropyridine is oxidized to 2,6-dichloropyridine-N-oxide. It is appreciated that 2,6-dichloropyridine-N-oxide can be present in the form of a salt, for example trifluoroacetic acid salt. The molar ratio of 2,6-dichloropyridine to hydrogen peroxide is between about 1:1 and about 1:8, advantageously between about 1:1 and about 1:4, more advantageously between about 1:1 and about 1:2. In one embodiment, trifluoroacetic acid is used both as a solvent and a catalyst for the oxidation reaction. In another embodiment, a solvent other than trifluoroacetic acid is utilized in the oxidization process. Suitable solvents include but are not limited to acetic acid, phthalic acid, maleic acid, chlorobenzoic acid, propionic acid and butyric acid. The molar ratio of 2,6-dichloropyridine relative to trifluoroacetic acid is between about 1:1 and about 1:50, preferably between about 1:3 and about 1:15, more advantageously between about 1:4 and about 1:12.

The oxidation temperature of step (a) is from about 20° C. to about 150° C., advantageously, from about 50° C. to about 100° C., more advantageously from about 60° C. to about 70° C. The oxidation of step (a) may be conducted under sub-atmospheric, atmospheric or super-atmospheric pressure. In one embodiment, the oxidation is conducted at atmospheric pressure. The oxidation time may vary from 1 hour to 48 hours, advantageously from 1 hour to 10 hours, more advantageously from 2 hours to 5 hours.

The oxidation reaction in step (a) produces a first intermediate containing (1) trifluoroacetic acid, and (2) 2,6-dichloropyridine-N-oxide. It is appreciated that 2,6-dichloropyridine-N-oxide may be present in the form of trifluoroacetic acid salt. In one embodiment, the crude product also contains unreacted 2,6-dichloropyridine.

A portion of the excess trifluoroacetic acid can be removed under reduced pressure. However, it was observed that not all the trifluoroacetic acid can be removed. Applicants surprisingly found that after adding sulfuric acid to the first intermediate, essentially all of the trifluoroacetic acid can be removed efficiently under reduced pressure such as distillation. By "essentially all" herein is meant that more than 90 wt %, advantageously more than 92 wt %, more advantageously, more than 99 wt % of trifluoroacetic acid based on the total weight of the trifluoroacetic acid is removed. For the purposes of the invention, it is appreciated that sulfuric acid can be added to the first intermediate either after a portion of the excess trifluoroacetic acid is removed or before any trifluoroacetic acid is removed. In one embodiment, for every mole of 2,6-dichloropyridine-N-oxide formed, at least 0.5 molar, advantageously from 0.5 molar to 3.0 molar equivalent of sulfuric acid is added. In another embodiment, for every mole of 2,6-dichloropyridine initially used to make the 2,6-dichloropyridine-N-oxide, at least 0.5 molar, advantageously from 0.5 to 1.0 molar equivalent of sulfuric acid is used.

In one embodiment, after removing trifluoroacetic acid, the process of the invention provides a composition containing 2,6-dichloropyridine-N-oxide and/or salts thereof, wherein the composition is essentially free of trifluoroacetic acid. By "essentially free" herein is meant that less than 10 wt %, advantageously less than 8 wt %, more advantageously less than 2 wt % of trifluoroacetic acid is present.

Without being bound by any theory, it is believed that in the first intermediate, trifluoroacetic acid forms a salt with 2,6-dichloropyridine-N-oxide, thus making it difficult to be removed. By adding sulfuric acid to the first intermediate, sulfuric acid forms a salt with 2,6-dichloropyridine-N-oxide, thus liberating trifluoroacetic acid, which can be sequentially removed.

After trifluoroacetic acid is removed, unreacted 2,6-dichloropyridine, if present in the composition produced at step (c) of the present process, can be precipitated out by pouring the composition into water. The precipitated 2,6-dichloropyridine can then be filtered off providing an aqueous composition containing 2,6-dichloropyridine-N-oxide and/or salts thereof. The composition is stable and can be stored at room temperature for an extended period of time. It can be used to prepare 1-hydroxy-6-substituted pyridone of Formula (I). However, it is appreciated that the 2,6-dichloropyridine-N-oxide-containing composition can also be used for other purposes.

The trifluoroacetic acid recovered from the oxidation process can be reused. In some embodiments, the trifluoroacetic acid recovered from the oxidation contains water. Advantageously, water can be removed from the trifluoroacetic acid/water mixture by first adding sulfuric acid to the mixture than removing trifluoroacetic acid from the mixture under reduced pressure, for example, flash distillation. The recovered trifluoroacetic acid can be reused without having a negative impact on the formation of 2,6-dichloropyridine-N-oxide and/or salts thereof.

In step (d), 2,6-dichloropyridine-N-oxide and/or salts thereof from step (c), advantageously but not necessarily as an aqueous solution, can react with a compound of Formula (II) in the presence of a base to produce a compound of Formula (III). In one embodiment, the 2,6-dichloropyridine-N-oxide is present in the form of a salt and is neutralized first before reacting with the compound of Formula (II) and a base.

Suitable bases includes but are not limited to sodium hydroxide, potassium hydroxide, and combinations thereof. The molar ratio of the base:the compound of Formula (II):2,6-dichloropyridine-N-oxide and/or salts thereof is between about 1:2:1 and about 10:20:1, advantageously, about 3.5:3.5:1.

Applicants surprisingly found that when the compound of Formula (II) is used in an amount of at least 3 molar equivalents to the 2,6-dichloropyridine-N-oxide and/or salts thereof in the presence of an approximately equivalent molar amount of base, the yield of the final product 1-hydroxy-6-substituted pyridone produced at step (e) is greatly improved and the pyridone can be made with high purity.

The suitable reaction temperature for converting 2,6-dichloropyridine-N-oxide and/or salts thereof to the compound of Formula (III) is between about 10° C. and about 150° C., advantageously between about 15° C. and about 100° C., more advantageously between about 20° C. and about 40° C.

The compound of Formula (III) can be converted to the 1-hydroxy-6-substituted pyridone of Formula (I) by heating the compound of Formula (III) at an elevated temperature. Suitable temperature ranges between about 30 to about 200° C., advantageously between about 50 and 150° C., more advantageously between about 75 and 125° C.

After the reaction is completed, the pyridone product, namely the compound of formula (I), can be precipitated out by adding water to the reaction mixture. In one embodiment, the excess amount of compound of Formula (II), such as octanol, is removed, for example, by distillation, before water is added. The recovered compound of Formula (II) can be reused to make the pyridones. The precipitated product has high purity and can be obtained by filtration. No further purification is needed.

In one embodiment, the aqueous solution containing 2,6-dichloropyridine-N-oxide and/or sulfuric acid salt thereof prepared from the process of the invention is first neutralized with a base, then treated with octanol. Water is removed azeotropically. Then the mixture is treated with a base such as sodium hydroxide at a temperature ranging from 20° C. to 100° C. for a period of time to provide 2,6-di(octyloxy)pyridine-N-oxide. The ratio of base:octanol:2,6-dichloropyridine-N-oxide is about 3.5:3.5:1.

After the reaction is done, an excess of water is then added to the reaction mixture and octanol is removed azeotropically at a temperature of between 70 and 150° C. During the process, 2,6-di(octyloxy)pyridine-N-oxide is converted to 1-hydroxy-6-(octyloxy)pyridine-2(1H)-one, which is precipitated out from the reaction mixture by adjusting the pH of the reaction mixture to between about 0.5 and about 6.

The following examples are intended to illustrate, but in no way limit the scope of the present invention. All parts and percentages are by weight and all temperatures are in degrees Celsius unless explicitly stated otherwise. All publications disclosed herein are incorporated by reference in their entireties.

EXAMPLES

Example 1 Preparation of 2,6-dichloropyridine-N-oxide 2,6-Dichloropyridine (338 g, 2.29 mol) was charged to a 5 liter jacketed reactor flask. To this, trifluoroacetic acid (1695 g, 14.9 mol) was added. This mixture was mechanically stirred and solution occurred within minutes. The solution was warmed to 59° C. To the warm solution, 50% hydrogen peroxide (157 g, 2.77 mol) was added over a period of 120 minutes. A slight exotherm occurred to a temperature of about 65° C. The reaction was then held at 65° C. for an additional 3 hours. The solution was collected and cooled. To the solution, sulfuric acid (224.6 g, 2.29 mol) was added. The majority of the trifluoroacetic acid (95-98%) was removed under reduced pressure on the roto-evaporator. The resulting mixture was then poured into water to precipitate unreacted 2,6-dichloropyridine. The 2,6-dichloropyridine was filtered off to give a solution of about 8% 2,6-dichloropyridine-N-oxide. The recovered 2,6-dichloropyridine can be reused in the next oxidation. The resulting aqueous solution of 2,6-dichloropyridine-N-oxide was stable for weeks and can then be used without further purification in the next reaction. A typical analysis of the solution showed 8.2% N-oxide, 83.6% water, 3.8% trifluoroacetic acid, 6.3% sulfuric acid and 0.14% 2,6-dichloropyridine.

Example 2 Preparation of 1-hydroxy-6-(octyloxy)pyridin-2(1H)-one 620 g of the aqueous solution of 2,6-dichloropyridine-N-oxide (50.8 g, 0.31 mol) was charged to a one liter round bottom flask and mechanically stirred. The strongly acidic solution was cooled to less than 20° C. To this 50% NaOH was added until the pH of the solution was 3.5-4.0. To this mixture 1-octanol (141.3 g, 1.09 mol) was added. The mixture was heated and refluxed into a Dean-Stark trap. Water was removed azeotropically from the reaction mixture via the Dean-Stark trap while the octanol was returned to the reaction flask. Water was removed until the boiling point of the reaction mixture was between 110° C.-120° C. At this point, 95 to 98% of the water had been removed. The resulting solution was cooled to less than 20° C. To the mixture, 50% NaOH (86.8 g, 1.09 mol) was added slowly over 60 minutes, keeping the temperature under 30° C. At this point a mixture of 2-chloro-6-(octyloxy)pyridine-N-oxide and 2,6-di(octyloxy)pyridine-N-oxide have been formed. After addition, the reaction was warmed to 40° C. and held at this temperature for 90-120 minutes. HPLC analysis showed mainly 2,6-di(octyloxy)pyridine-N-oxide was present with possibly a small amount of 2-chloro-6-(octyl-oxy)pyridine-N-oxide. The reaction was then heated to 100° C. for 60 to 90 minutes. This converts the remainder of 2-chloro-6-(octyloxy)pyridine-N-oxide to 2,6-di(octyloxy)pyridine-N-oxide and all of 2,6-di(octyloxy)pyridine-N-oxide to 1-hydroxy-6-(octyloxy)pyridine-2(1'-1)-one. The reaction was then diluted with 2500-3000 g of water. This mixture was then refluxed into a Dean-Stark trap and any excess octanol was removed azeotropically until no more octanol was visibly seen entering the Dean-Stark trap. The strongly basic aqueous mixture was then mechanically stirred, cooled to less than 30° C. The mixture was treated with 20 g of a 12.5% sodium hypochlorite solution. This was stirred 15 minutes and sulfuric acid was then added until the pH of the mixture was between 1 and 4. The resulting solid was filtered, washed with water and air dried under a dam for 2 hours. Obtained 67.2 g of active 1-hydroxy-6-(octyloxy)-pyridine-2(1H)-one (90.6% yield from the N-oxide). NMR was consistent with the expected structure and a sample matches a known sample by HPLC which showed one major peak.

Example 3 Recovery and Purification of Trifluoroacetic Acid

The oxidation mixture of trifluoroacetic acid, water, 2,6-dichloropyridine-N-oxide and unreacted 2,6-dichloropyridine was treated first with 0.9 to 2 molar equivalents of sulfuric acid and then placed on the rotary evaporator under reduced pressure at 25 to 30 inches of mercury (85 to 102 kPa). The bath was heated initially to 60° C. and slowly increased to 115° C. Removal of the trifluoroacetic acid continues until small amounts of 2,6-dichloropyridine-N-oxide begins to precipitate out. From this mixture unreacted 2,6-dichloropyridine was recovered and the 2,6-dichloropyridine-N-oxide solution was prepared.

The Trifluoroacetic acid that was collected contained water which if used without removing would be detrimental to yields of future oxidations. The amount of water present was determined by traditional Karl Fischer analysis. After determining the weight of the water present, at least two parts of sulfuric acid for every part of water was added to the mixture. The addition of the sulfuric acid breaks the water/trifluoroacetic acid azeotrope and allows fractional distillation of the trifluoroacetic acid to be carried out at a temperature of 72° C.

In one example a mixture of 57.1% trifluoroacetic acid, 14.3% water and 28.6% sulfuric acid were continuously fed into a reactor at atmospheric pressure and 1.3 g per minute. The pot temperature was kept at 125° C. allowing for trifluoroacetic acid to be removed overhead at a temperature of 68° C. This was continued for 5 hours at which time 94% of the theoretical trifluoroacetic acid was collected. Sodium hydroxide titration showed the acid to be free of water.

Example 4 Recovery of Octanol

During the preparation of 2,6-di(octyloxy)pyridine-N-oxide, 3.5 molar equivalents of octanol was employed. After the final product, 1-hydroxy-6-(octyloxy)pyridine-2(1H)-one, was produced, only 1 molar equivalent was actually consumed. The remaining octanol was recovered and reused. After heating at 100° C. in the preparation of 1-hydroxy-6-(octyloxy)-pyridine-2(1H)-one, the reaction mixture was diluted 10 to 15 times by weight with water. The mixture was heated to near 100° C. at atmospheric pressure and an azeotrope of water and octanol is refluxed into a Dean-Stark trap. The water is returned to the reaction mixture and the octanol is recovered and reused. In one example, 99.5% of the theoretical octanol is recovered, containing about 5% water.

Example 5 Preparation of 1-hydroxy-6-(octyloxy) pyridin-2(1H)-one (V) Using Recovered Octanol 620 g of the aqueous solution of 2,6-dichloropyridine-N-oxide (51.0 g, 0.31 mol) was charged to a one liter round bottom flask and mechanically stirred. The strongly acidic solution was cooled to less than 20° C. To this 50% NaOH was added until the pH of the solution is 3.5-4.0. To this mixture 1-octanol (149.5 g, containing 5.1% water) (141.3 g, 1.09 mol) was added. The mixture was heated and refluxed into a Dean-Stark trap. The water was removed azeotropically from the reaction mixture via the Dean-Stark trap while the octanol was returned to the reaction flask. Water was removed until the boiling point of the reaction mixture was 120° C. At this point, 95 to 98% of the water had been removed. The resulting solution was cooled to less than 20° C. To the mixture, 50% NaOH (86.8 g, 1.09 mol) was added slowly over 60 minutes, keeping the temperature under 30° C. After addition, the reaction was warmed to 40° C. and held at this temperature for 90-120 minutes. The reaction was then heated to 100° C. for 60 minutes. The reaction mixture was then diluted with 2500-3000 g of water. This mixture was then refluxed into a Dean-Stark trap and any excess octanol was removed azeotropically until no more octanol was visibly seen entering the Dean-Stark trap. The strongly basic aqueous mixture was then mechanically stirred, cooled to less than 30° C. and treated with 20 g of a 12.5% sodium hypochlorite solution. The resultant was stirred for 15 minutes and sulfuric acid was then added until the pH of the mixture is 2.5 to 3. The resulting solid was filtered, washed with water and air dried under a dam for 2 hours. Obtained 67.2 g of active 1-hydroxy-6-(octyloxy) pyridine-2(1H)-one (90.6% yield from the N-oxide). NMR was consistent with the expected structure and a sample matched a known sample by HPLC which showed one major peak.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:
1. A process for producing the compound of the structural formula (I)

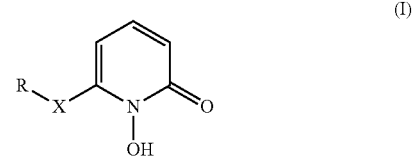

(I)

wherein X is oxygen or sulfur, each R is independently a substituted or unsubstituted linear hydrocarbyl group having between 3 and 18 carbon atoms, the process comprising the steps of:
(a) reacting 2,6-dichloropyridine with hydrogen peroxide in the presence of an acid catalyst at a first temperature to produce a first intermediate containing (1) the acid catalyst and (2) 2,6-dichloro-pyridine-N-oxide and/or salts thereof;
(b) adding an acid having a pKa number lower than the pKa number of the acid catalyst to the first intermediate to provide a second intermediate;
(c) removing the acid catalyst from the second intermediate to provide a composition containing 2,6-dichloropyridine-N-oxide and/or salts thereof;
(d) reacting 2,6-dichloropyridine-N-oxide and/or salts thereof from step (c) with a compound having the structural formula (II), and a base, optionally in the presence of water or an organic solvent, at a second temperature to produce a compound of Formula (III); and
(e) heating the compound of Formula (III) at a third temperature thereby producing the compound of Formula (I), wherein the compounds of Formula (II) and Formula (III) are R—X—H (Formula II)

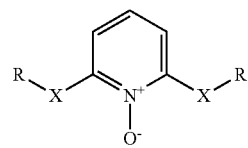

(Formula III)

wherein each R in Formulae (II) and (III) is independently a substituted or unsubstituted linear hydrocarbyl group having between 3 and 18 carbon atoms, and X is oxygen or sulfur, and
wherein the yield of the compound of Formula (I) from the 2,6-dichloropyridine-N-oxide and/or salts thereof is greater than 80%.

2. A process as defined in claim 1, wherein the acid catalyst comprises trifluoroacetic acid.

3. A process as defined in claim 1, wherein the acid comprises sulfuric acid.

4. A process for producing the compound of the structural formula (I)

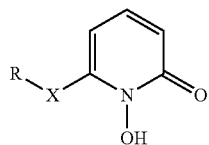
(I)

wherein X is oxygen or sulfur, each R is independently a substituted or unsubstituted linear hydrocarbyl group having between 3 and 18 carbon atoms, the process comprising the steps of:
(a) reacting 2,6-dichloropyridine with hydrogen peroxide in the presence of trifluoroacetic acid at a first temperature to produce a first intermediate containing (1) trifluoroacetic acid and (2) 2,6-dichloro-pyridine-N-oxide and/or salts thereof;
(b) adding sulfuric acid to the first intermediate to provide a second intermediate;
(c) removing trifluoroacetic acid from the second intermediate to provide a composition containing 2,6-dichloropyridine-N-oxide and/or salts thereof;
(d) reacting 2,6-dichloropyridine-N-oxide and/or salts thereof from step (c) with a compound having the structural formula (II), and a base, optionally in the presence of water or an organic solvent, at a second temperature to produce a compound of Formula (III); and
(e) heating the compound of Formula (III) at a third temperature thereby producing the compound of Formula (I), wherein the compounds of Formula (II) and Formula (III) are:

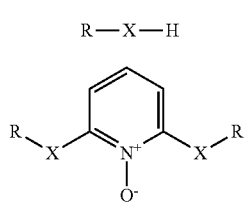

(Formula II)
(Formula III)

wherein each R in Formulae (II) and (III) is independently a substituted or unsubstituted linear hydrocarbyl group having between 3 and 18 carbon atoms, and X is oxygen or sulfur, and
wherein the yield of the compound of Formula (I) from the 2,6-dichloropyridine-N-oxide and/or salts thereof is greater than 80%.

5. A process according to claim 4 wherein R is octyl in Formulae (I), (II) and (III).

6. A process according to claim 4 wherein the first temperature is between 20° C. and 150° C.

7. A process according to claim 4 wherein the second temperature is between 10° C. and 150° C.

8. A process according to claim 4 wherein the third temperature is between 30° C. and 200° C.

9. A process according to claim 4 wherein at step (d) the molar ratio of 2,6-dichloropyridine-N-oxide and/or salts thereof relative to the compound of Formula (II) is equal to or greater than 1:5.

10. A process according to claim 4 wherein the base used at step (d) is sodium hydroxide, potassium hydroxide or combinations thereof.

11. A process according to claim 4 wherein the composition obtained at step (c) contains less than 10 wt % of trifluoroacetic acid based on the total weight of the composition.

12. A process according to claim 11 wherein the composition contains less than 2 wt % of trifluoroacetic acid based on the total weight of the composition.

13. A process according to claim 11 wherein the composition contains less than 8 wt % of trifluoroacetic acid based on the total weight of the composition.

14. A process according to claim 4 wherein at step (a) the molar ratio of 2,6-dichloropyridine:hydrogen peroxide is between 1:1 and 1:8, and the molar ratio of 2,6-dichloropyridine:trifluoroacetic acid is between 1:1 and 1:50.

15. A process according to claim 4 wherein at step (c) the trifluoroacetic acid is removed under reduced pressure.

16. A process according to claim 4 wherein the first intermediate contains 2,6-dichloropyridine, and wherein the process additionally comprises the steps of:
(i) contacting the composition obtained from step (c) with water to precipitate 2,6-di-chloropyridine; and
(ii) removing 2,6-dichloropyridine from the composition of step (i) by filtration to provide a composition containing 2,6-dichloropyridine-N-oxide and/or salts thereof.

17. A process according to claim 1, wherein R is independently a substituted or unsubstituted linear hydrocarbyl group having between 5 and 10 carbon atoms.

18. A process according to claim 4, wherein R is independently a substituted or unsubstituted linear hydrocarbyl group having between 5 and 10 carbon atoms.

19. A process for producing the compound of the structural formula (I)

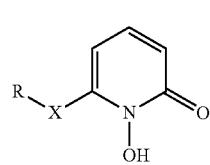
(I)

wherein X is oxygen or sulfur, each R is independently a substituted or unsubstituted hydrocarbyl group having between 1 and 20 carbon atoms, the process comprising the steps of:
(a) reacting 2,6-dichloropyridine with hydrogen peroxide in the presence of an acid catalyst at a first temperature to produce a first intermediate containing (1) the acid catalyst and (2) 2,6-dichloro-pyridine-N-oxide and/or salts thereof;
(b) adding an acid having a pKa number lower than the pKa number of the acid catalyst to the first intermediate to provide a second intermediate;
(c) removing the acid catalyst from the second intermediate to provide a composition containing 2,6-dichloropyridine-N-oxide and/or salts thereof;
(d) reacting 2,6-dichloropyridine-N-oxide and/or salts thereof from step (c) with a compound having the structural formula (II), and a base, optionally in the presence of water or an organic solvent, at a second temperature to produce a compound of Formula (III), wherein the molar ratio of the base to the compound having the structural formula (II) to the 2,6-dichloropyridine-N-oxide and/or salts thereof is from 1:2:1 to 10:20:1; and (e) heating the compound of Formula (III) at a third temperature thereby producing the compound of Formula (I), wherein the compounds of Formula (II) and Formula (III) are:

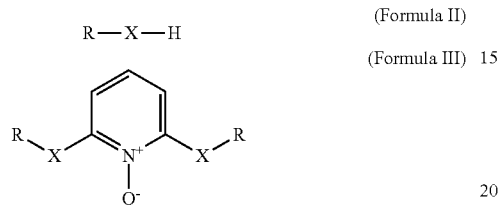

(Formula II)

(Formula III)

wherein each R in Formulae (II) and (III) is independently a substituted or unsubstituted hydrocarbyl group having between 1 and 20 carbon atoms, and X is oxygen or sulfur, and wherein the yield of the compound of Formula (I) from the 2,6-dichloropyridine-N-oxide and/or salts thereof is greater than 80%.

20. A process according to claim 19, wherein the molar ratio of the base to the compound having the structural formula (II) to the 2,6-dichloropyridine-N-oxide and/or salts thereof is from 1:2:1 to 3.5:3.5:1.

21. A process according to claim 19, wherein the acid catalyst comprises trifluoroacetic acid, the acid comprises sulfuric acid, or a combination thereof.

22. A process for producing the compound of the structural formula (I)

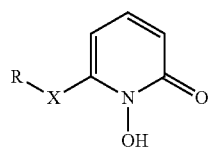

(I)

wherein X is oxygen or sulfur, each R is independently a substituted or unsubstituted hydrocarbyl group having between 1 and 20 carbon atoms, the process comprising the steps of:

(a) reacting 2,6-dichloropyridine with hydrogen peroxide in the presence of trifluoroacetic acid at a first temperature to produce a first intermediate containing (1) trifluoroacetic acid and (2) 2,6-dichloro-pyridine-N-oxide and/or salts thereof;

(b) adding sulfuric acid to the first intermediate to provide a second intermediate;

(c) removing trifluoroacetic acid from the second intermediate to provide a composition containing 2,6-dichloropyridine-N-oxide and/or salts thereof;

(d) reacting 2,6-dichloropyridine-N-oxide and/or salts thereof from step (c) with a compound having the structural formula (II), and a base, optionally in the presence of water or an organic solvent, at a second temperature to produce a compound of Formula (III), wherein the molar ratio of the compound having the structural formula (II) to the 2,6-dichloropyridine-N-oxide and/or salts thereof is from 3:1 to 15:1; and (e) heating the compound of Formula (III) at a third temperature thereby producing the compound of Formula (I), wherein the compounds of Formula (II) and Formula (III) are:

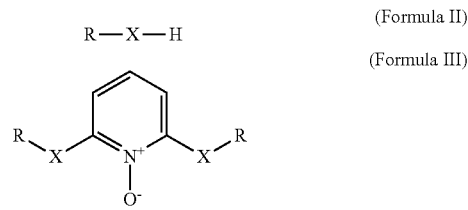

(Formula II)

(Formula III)

wherein each R in Formulae (II) and (III) is independently a substituted or unsubstituted hydrocarbyl group having between 1 and 20 carbon atoms, and X is oxygen or sulfur, and wherein the yield of the compound of Formula (I) from the 2,6-dichloropyridine-N-oxide and/or salts thereof is greater than 80%.

23. A process according to claim 22 wherein R is octyl in Formulae (I), (II) and (III).

* * * * *